United States Patent [19]
White

[11] Patent Number: 5,999,851
[45] Date of Patent: Dec. 7, 1999

[54] ATRIAL DEFIBRILLATION SYSTEM HAVING PATIENT SELECTABLE ATRIAL FIBRILLATION DETECTION

[75] Inventor: Harley G. White, Carnation, Wash.

[73] Assignee: Cardiac Pacemakers, Inc., St. Paul, Minn.

[21] Appl. No.: 09/060,723

[22] Filed: Apr. 15, 1998

[51] Int. Cl.[6] .................................................. A61N 1/39
[52] U.S. Cl. ...................................................... 607/5
[58] Field of Search .......................... 607/5, 32; 128/903

[56] References Cited

U.S. PATENT DOCUMENTS

| | | | |
|---|---|---|---|
| 5,311,449 | 5/1994 | Adams ..................................... | 364/514 |
| 5,336,245 | 8/1994 | Adams et al. ............................. | 607/32 |
| 5,441,519 | 8/1995 | Sears ........................................... | 607/5 |
| 5,464,431 | 11/1995 | Adams et al. . | |
| 5,490,862 | 2/1996 | Adams et al. . | |
| 5,522,850 | 6/1996 | Yomtov et al. .............................. | 607/5 |
| 5,674,248 | 10/1997 | de Coriolis et al. ........................ | 607/5 |
| 5,755,737 | 5/1998 | Prieve et al. .................................. | 607/5 |

*Primary Examiner*—William E. Kamm
*Assistant Examiner*—Carl H. Layno
*Attorney, Agent, or Firm*—Foley & Lardner

[57] ABSTRACT

An atrial defibrillation system includes an implantable atrial defibrillator having an atrial defibrillation detector for detecting atrial fibrillation and a cardioverter for cardioverting the atria of a heart. The implantable atrial defibrillator further includes a receiver for receiving commands from an external nonimplanted transmitter. A nonimplantable communication device includes a transmitter for transmitting a command to the receiver. The command causes only the atrial fibrillation detector to be activated resulting only in the detection for atrial fibrillation without committing to atrial fibrillation cardioversion should atrial fibrillation be detected.

9 Claims, 2 Drawing Sheets

ATRIAL DEFIBRILLATION SYSTEM HAVING PATIENT SELECTABLE ATRIAL FIBRILLATION DETECTION

BACKGROUND OF THE INVENTION

The present invention generally relates to a defibrillation system including an atrial defibrillator for applying cardioverting electrical energy to the atria of a human heart in need of cardioversion. The present invention is more particularly directed to such a system having a portable communication device operable by a patient for selectably initiating atrial fibrillation detection without committing to atrial cardioverting therapy.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart, and may even experience dizziness or even loss of consciousness.

Atrial fibrillation occurs suddenly, and many times can only be corrected by a discharge of electrical energy to the heart. Implantable atrial defibrillators have become a reality to provide relief to patients suffering from occurrences of atrial fibrillation.

For example, implantable atrial defibrillators and lead systems which exhibit complete automatic operation are fully described in U.S. Pat. No. 5,282,837, issued Feb. 1, 1994, for "Improved Atrial Defibrillator and Method," U.S. Pat. No. 5,350,404, issued Sep. 27, 1994, for "Lead System for Use with an Atrial Defibrillator and Method," and U.S. Pat. No. 5,207,219, issued May 4, 1993, for "Atrial Defibrillator and Method for Providing Interval Timing Prior to Cardioversion," all of which patents are assigned to the assignee of the present invention and incorporated herein by reference. Each of these patents discloses and claims an implantable atrial defibrillator wherein atrial fibrillation is automatically detected and, when needed, cardioverting electrical energy is applied to the atria to terminate the atrial fibrillation episode and return the heart to normal sinus rhythm.

As with any implantable device, it would be desirable to be able to provide the patient with some manual control for the implanted device. For example, implantable pacemakers known in the art may be totally deactivated by placing a magnet over the implant site. The magnetic field of the magnet causes a reed switch within the implanted device to remain either open or closed as long as the magnet is held there. Other magnet modes are known for checking the power levels of the implanted device battery, for example.

While magnets have proven effective in the past, they are not convenient to use. First of all, such magnets are heavy and, in most uses, rather large, making them difficult to carry in a pocket or purse. Also, because the magnets produce a magnetic field, they can erase dictation or other type of audio tape to which they may come into close proximity within a purse or pocket. Under such conditions, they can also erase the magnetic strips on credit and bank cards. They would further erase floppy disks for computers.

Providing some manual control over an implanted atrial defibrillator is described in U.S. Pat. No. 5,490,862. There, a magnet is described for generating external commands which cause the defibrillator to enter an atrial fibrillation detection and committed therapy sequence. A magnet is certainly effective for such use. However, in addition to the drawbacks previously mentioned, magnets do not provide any means for feedback to inform the patient that the implanted device is acting upon the external command. An acknowledgment of receipt of a command and the fact that the implant is implementing the command would be important feedback to patients. This is especially true if the patient is attempting to have the implanted device initiate required therapy.

In answer to the problems resulting from the use of magnets in such systems, an atrial defibrillation system including an external communication device dimensioned to be hand-held is disclosed and claimed in U.S. Pat. No. 5,674,249 which issued on Oct. 7, 1997 for "Atrial Defibrillation System Having A Portable Communication Device," and which is incorporated herein by reference. The portable communication device there disclosed includes an RF transmitter for transmitting a command signal to the implantable defibrillator. The implantable defibrillator includes a receiver for receiving the command signals and performs a task responsive to receipt of the command signal. An RF transmitter within the implantable device transmits an acknowledgment signal back to the portable communication device upon receipt of the command signal. The portable communication device further includes a receiver which receives the acknowledgment signal and provides a perceptible indication responsive to receipt of the acknowledgment signal to the patient. In this way, the patient knows that the command was received and that the implanted device is performing the desired task.

While the last two mentioned atrial defibrillation systems go a long way towards providing effective and positive control of an implantable atrial defibrillator by the patient, they do not provide a complete answer. For example, they provide for very limited operational modalities of an automatic mode, a patient activated mode, and a combination of these two modalities. In all of these modalities, the patient is committed to cardioverting therapy if atrial fibrillation is detected. In the automatic mode, atrial fibrillation detections most often occur when the patient is not in atrial fibrillation. Many atrial fibrillation patients are highly symptomatic when experiencing atrial fibrillation. Automatic detection for these patients can represent unwarranted depletion of the defibrillator power source. Further, a patient may not be in a position to receive cardioverting therapy at a time when the committed therapy is to be delivered. At other times, a patient may simply want to confirm the absence of atrial fibrillation or be able to determine that the atrial fibrillation detector of the patient's defibrillator agrees with patient's perception of the arrhythmia. Hence, there is a need in the art for an atrial defibrillation system which enables a patient to select and activate atrial fibrillation detection without committing to cardioverting therapy.

SUMMARY OF THE INVENTION

The invention provides an atrial defibrillation system including an implantable atrial defibrillator including an atrial fibrillation detector for detecting atrial fibrillation and a cardioverter for cardioverting the atria of a heart. The implantable atrial defibrillator further includes a receiver for receiving commands from an external nonimplanted transmitter. The system further includes a nonimplantable communication device including a transmitter for transmitting a command to the receiver for activating only the atrial fibrillation detector to cause the atrial fibrillation detector to detect for atrial fibrillation.

The present invention further provides an atrial defibrillation system including an implantable atrial defibrillator including an atrial fibrillation detector for detecting fibrillation of a patient's atria, an atrial cardioverter for applying cardioverting electrical energy to the patient's atria, a receiver for receiving operation commands transmitted from an external transmitter, and a mode selecting stage for causing the defibrillator to operate in a first mode of operation wherein only the atrial fibrillation detector is activated to detect for atrial fibrillation or in a second mode of operation wherein the atrial fibrillation detector is activated to detect for atrial fibrillation and then the cardioverter is activated for applying cardioverting electrical energy to the patient's atria if atrial fibrillation is detected. The system further includes a nonimplantable communication device dimensioned to be hand-held and operable by the patient including a transmitter for selectively transmitting a first operation command to cause the mode selector stage to render the implantable atrial defibrillator in the first mode of operation and a second operation command to cause the mode selector stage to render the implantable atrial defibrillator in the second mode of operation.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
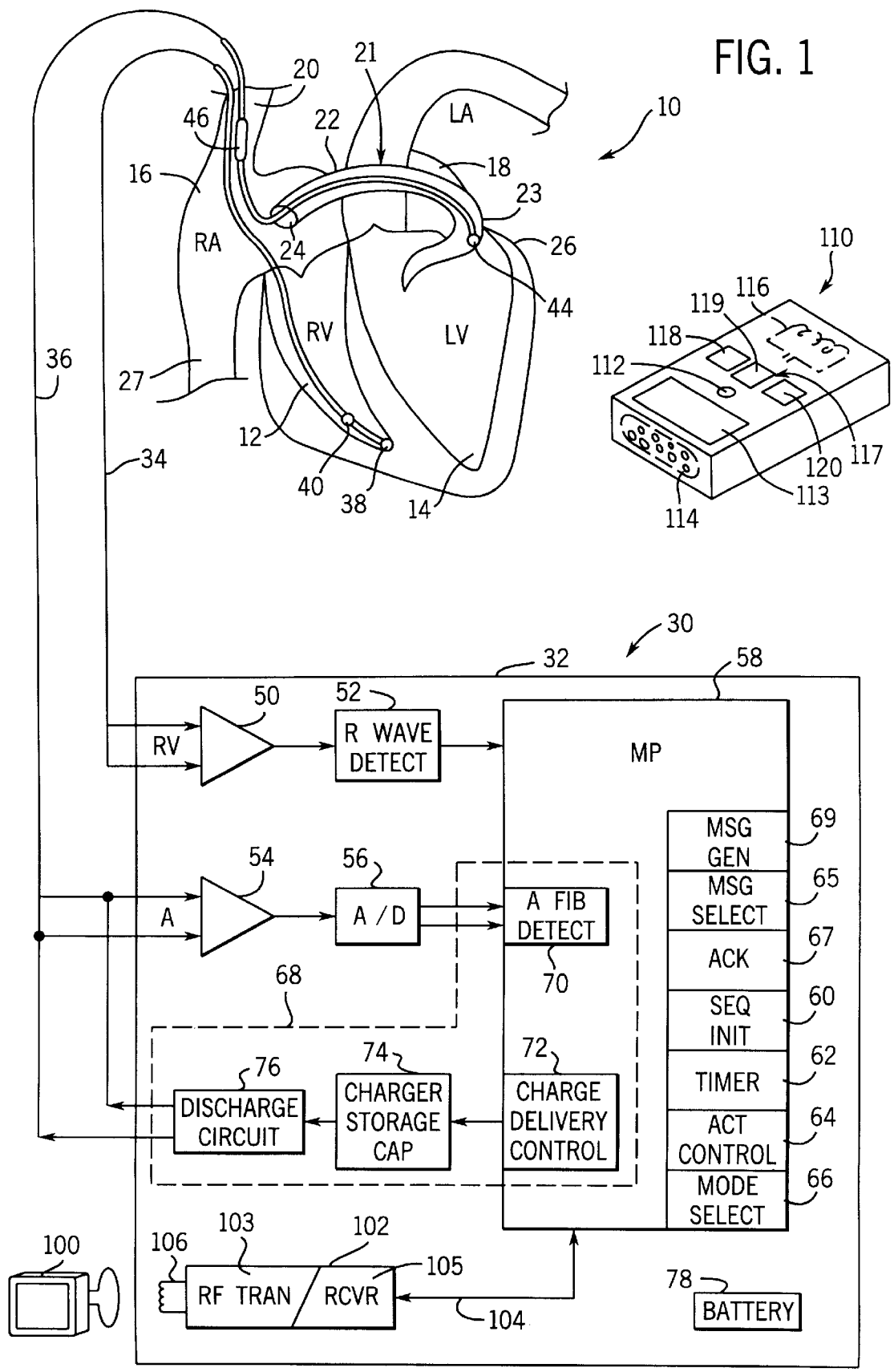
FIG. 1 is a block diagram of an atrial defibrillation system embodying the present invention.

Referring now to FIG. 1, it illustrates an atrial defibrillation system 10 embodying the present invention including an implantable atrial defibrillator 30 shown in association with a schematically illustrated human heart in need of atrial fibrillation monitoring and potential cardioversion and a portable, hand-holdable external communication device 110. The portions of the heart illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart. The electrodes 38 and 40 permit bi-polar sensing of ventricular activations in the right ventricle. As illustrated, the lead 34 is preferably fed through the superior vena cava 20, into the right atrium 16 and then into the right ventricle 12, as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16.

The first electrode 44 together with the second electrode 46 provide bi-polar sensing of heart activity in the atria 16 and 18. The first electrode 44 and the second electrode 46 further provide for the delivery of defibrillating or cardioverting electrical energy to the atria.

Within the enclosure 32, the atrial defibrillator 30 includes a first sense amplifier 50, an R wave detector 52, and a second sense amplifier 54. The first sense amplifier 50 and the R wave detector 52, together with electrodes 38 and 40 of lead 34, sense ventricular activations of the right ventricle 12. The second sense amplifier 54, together with the first electrode 44 and second electrode 46 of the second lead 36, detect atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog-to-digital converter 56 which converts the analog signal representative of the atrial activity of the heart being detected to digital samples for further processing in a manner to be described hereinafter.

The enclosure 32 of the atrial defibrillator 30 further includes a microprocessor 58. The implementation of the microprocessor 58 in accordance with this embodiment of the present invention results in a plurality of operating stages. The stages include a sequence initiating stage 60, a timer 62, an activation control stage 64, a message select stage 65, a mode select stage 66, an acknowledgment stage 67, a message generator stage 69, an atrial fibrillation detector stage 70, and a charge and delivery control stage 72. Each operating stage performs a respective different operation.

The microprocessor 58 is arranged to operate in conjunction with a memory (not shown) which may be coupled to the microprocessor 58 by a multiple-bit address bus (not shown) and a bi-directional multiple-bit data bus (not shown). This permits the microprocessor 58 to address desired memory locations within the memory for executing write or read operations. During a write operation, the microprocessor stores data and operating parameters (such as a selected modality) in the memory at the addresses defined by multiple-bit addresses conveyed over the address bus and conveys the data to the memory over the multiple-bit data bus. During a read operation, the microprocessor 58 obtains data from the memory at the storage locations identified by the multiple-bit addresses provided over the address bus and receives the data from the memory over the bi-directional data bus.

For entering operating parameters into the microprocessor 58, such as mode selection, the microprocessor 58 receives programmable operating parameters, such as mode commands, from an external controller 100 which is external to the skin of the patient. The external controller 100 is arranged to communicate with a telemetry stage or receiver/transmitter 102 which includes a transmitter 103 and a receiver 105 and is coupled to the microprocessor 58 over a bi-directional bus 104. The receiver/transmitter 102 may be of the type well known in the art for conveying various information which it obtains from the microprocessor 58 to the external controller 100 or for receiving programming parameters, such as mode commands, from the external controller 100 which the receiver/transmitter 102 then conveys to the microprocessor 58 for storage in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One preferred communication system is disclosed, for example, in U.S. Pat. No. 5,342,408, which is incorporated herein by reference.

The transmitter 103 and receiver 105 of receiver/transmitter 102 may also communicate with the portable communication device 110. However, the control commands which may be provided by the device 110 are preferably vastly limited as compared to the control commands which may be derived from the external programmer. To that end, the control commands which may be transmitted from the device 110 are preferably simple mode select commands, a therapy sequence control command, and a status request control command. The mode select commands preferably set the defibrillator into one of a number of modalities wherein each modality is determined and controlled by parameters which can only be selected by a physician operating the external programmer 100.

The acknowledgment stage 67 formats an acknowledgment message when the defibrillator 30 receives a command from the device 110. The acknowledgment message is transmitted by the transmitter/receiver 102 to cause an indicator, such as a light emitting diode 112 (LED) to provide a readily perceptible indication that the command was received. As will be seen hereinafter, the acknowledgment message may also cause a speaker 114 to produce an audible speech message acknowledging receipt of the command. This provides positive feed-back for the patient. The patient will positively know if the command was received and is being acted upon by the implanted device 30.

The atrial defibrillator 30 further includes an intervention sequencer 68 which includes a plurality of operating stages to perform an intervention sequence task including atrial fibrillation detection alone or atrial fibrillation detection and committed cardioversion of the atria if necessary. To that end, the intervention sequencer includes the previously mentioned atrial fibrillation detector 70 and charge and delivery control 72 operating stages, and further operating stages including a charger and storage capacitor circuit 74 and a cardioverter discharge circuit 76.

Lastly, the defibrillator 30 includes a depletable power source 78, such as a lithium battery. The battery 78, of course, provides power to the electrical components of the atrial defibrillator 30.

The communication device 110 of FIG. 1, includes an LED 112 to provide visual indications as described in the aforementioned U.S. Pat. No. 5,674,249. It further includes a liquid crystal display (LCD) 113, the speaker 114, the coil antenna 116, and a plurality of press switches 117 including press switches 118, 119, and 120. The LCD 114 may be used for displaying short messages indicating modalities available for selection, current modality, and receipt by the implanted device of a sequence command or modality selection. The speaker 114, as previously mentioned, is provided to provide audible speech messages or sounds. The coil antenna 116 may be used for both transmitting and receiving RF signals. Lastly, the push switches are provided for selecting a modality by pressing switch 118, for transmitting a status request command by pressing switch 119, and transmitting a sequence command by pressing switch 120.

Each intervention sequence is begun by the sequence initiating stage 60 receiving a sequence command. The sequence command is generated by the communication device 110 when the switch 120 is depressed to provide an RF signal to be received by the receiver 105 of receiver/transmitter 102. The received sequence command causes an interrupt to the microprocessor 58 whereby the sequence initiating stage 60 causes the intervention sequencer to perform the intervention sequence defined by the currently programmed modality of the defibrillator 30.

Each intervention sequence preferably begins with the sequence initiating stage 60 causing the atrial fibrillation detector 70 to determine if the atria are in need of cardioversion. This analysis is preferably performed on data obtained from sense amplifier 54 and analog-to-digital converter 56 and stored in the aforementioned memory (not shown) external to the microprocessor 58, but contained within the implantable enclosure 32. The atrial fibrillation detector 70 may alternatively be of the type which performs real time analysis of the data provided by the analog-to-digital converter 56. For purposes of the present invention, the atrial fibrillation detector is intended to include those elements which acquire the heart activity data required by the atrial fibrillation detector 70 for performing its analysis. Those elements may include the sense amplifier 54, the analog-to-digital converter 56 and further elements for storing the acquired data if the detection is based upon stored data.

If the atria are in fibrillation, and cardioverting therapy is committed, the charger and storage capacitor circuit 74 under control of the charge and delivery stage 72 charges its storage capacitor to a predetermined voltage level for cardioverting the atria of the patient's heart. When the capacitor of circuit 74 is charged, the charge and delivery control stage 72 then causes the discharge circuit 76 to discharge the storage capacitor within circuit 74 for a predetermined time to provide a controlled discharge of cardioverting electrical energy to the atria of the heart. To that end, the discharge circuit 76 is coupled to the first electrode 44 and the second electrode 46 of the second lead 36 for applying the cardioverting or defibrillating electrical energy to the atria. The discharge is preferably initiated in timed relation to an R wave detected by sense amplifier 50 and R wave detector 52. Interval timing prior to energy delivery is also preferably performed as taught in U.S. Pat. No. 5,207,219.

In addition to the acknowledgment messages generated by the acknowledgment stage 67, the message generator 69 is preferably capable of generating a message corresponding to the operation status of each operating stage of an intervention sequence. For example, when the initiating stage 60 initiates an intervention sequence, the message generator will formulate a status message to that effect for transmission to the portable communication device 110. A status message may be generated upon completion of atrial fibrillation detection and provide an indication of detection outcome. A status message may be generated when the storage capacitor of circuit 74 is fully charged to advise the patient that therapy is imminent. During capacitor charging it may generate a message to that effect if the patient transmits a status request during that time by depressing switch 119. As will be seen hereinafter, the status messages are decoded by the device 110 which then plays a corresponding, prestored, appropriate audible voice message.

The message selector stage 65 monitors the operating status of the various operating stages. It causes the message generator 69 to generate the appropriate status message.

The overall operation of the atrial defibrillator 30 is preferably carried out by first placing the atrial defibrillator 30 into one of a plurality of different modes of operation. The selectable modalities include an automatic mode, a patient activated mode, a combined automatic and patient activated mode and an atrial fibrillation detection only mode. To that end, at relatively short, predetermined time intervals, the RF transmitter/receiver 102 is activated to determine if either the external controller 100 or the communication device 110 is attempting to communicate with the implanted defibrillator 30. If a program mode control signal is being received, the mode select stage 66 will cause the acknowledge stage 67 to format and transmit an acknowledgment, decode the mode command and set the defibrillator 30 into the selected mode of operation.

If the atrial defibrillator 30 is set into the automatic mode by the mode select stage 66, the atrial defibrillator 30 will automatically, at predetermined times defined by timer 62, determine if the atria are in fibrillation. If the atria are in fibrillation, cardioverting electrical energy is applied to the atria until the atrial fibrillation episode is terminated or until a predetermined number of cardioversion attempts are made.

If the patient activated mode is selected, the sequence initiating stage 60 continuously detects for a sequence command generated from external to the patient. When the sequence command is received by the implanted device, the sequence initiating stage 60 causes the patient activated mode intervention sequence to be performed. The atrial fibrillation detector 70 first determines if the atria are in fibrillation and in need of cardioversion. If the atria are not in fibrillation, the process is terminated and the sequence initiating stage once again waits for another sequence command. However, if the atria are in fibrillation, cardioverting electrical energy is applied to the heart. After the cardioverting electrical energy is applied to the heart, the atrial fibrillation detector 70 determines if the atrial fibrillation episode has been terminated. If it has, the process is terminated and the sequence initiating stage once again waits for another sequence command. If the atrial fibrillation continues, the atria are once again cardioverted. This process continues until the atrial fibrillation episode is either terminated or until a predetermined number of cardioversion attempts have been made.

If the atrial defibrillator is programmed into the combined automatic and patient activated mode the sequence initiating stage 60 continuously waits for a sequence command or for the timer 62 to time out. When either occurs, the sequence initiating stage 60 will cause the intervention sequencer 68 to perform its intervention sequence as previously described.

Lastly, if in accordance with the present invention, the atrial defibrillator is programmed into the atrial fibrillation detection only mode, upon receipt of a sequence initiating command from the device 110, the atrial fibrillation detector only will be activated by the sequence stage 60 and the defibrillator will thus only detect for atrial fibrillation. If atrial fibrillation is detected, the patient will then be afforded the opportunity to reprogram the defibrillator into the patient activated mode for requesting and receiving cardioversion therapy. As previously mentioned, this modality and form of therapy may be desired by those patients who are highly symptomatic when an atrial fibrillation episode occurs. It would conserve battery power and afford the patient greater flexibility in managing the atrial arrhythmia.

To be more specific, and to further illustrate the present invention, assuming that the defibrillator has been programmed into the atrial fibrillation detection only mode, when the patient suspects that his/her heart is in atrial fibrillation, the patient depresses switch 119 to transmit a sequence initiation command. When the command is received by the receiver 105, the acknowledgement stage 67 formulates an acknowledgement message that the command was received and is being acted upon. In accordance with the present invention, the acknowledgment message causes the device 110 to play back a suitable audible voice message. Of course, additional indicators may also be used, such as the LED 112.

Now the sequence stage 60 causes the atrial fibrillation detection to begin. If the detection is based upon acquired and stored heart activity data, the message generator 69 responsive to the message select stage 65, generates a status message of data acquisition to cause the device 110 to provide an audible voice or speech message to that effect. Once the data is acquired and stored, it is then analyzed. A status message that data analysis is being performed may be transmitted at this time automatically or if a status request is made by the patient with device 110. When the detection is complete, the outcome result is then communicated as a status message to the patient which will cause a perceptible indication by the device 110 such as by lighting the LED 112 or causing a suitable audible voice or speech message to be played back by the device 110.

If the patient is in atrial fibrillation, the defibrillator will not go directly to provision of cardioversion therapy. Instead, it is up to the patient whether or not cardioversion will take place at that time. Here, the audible voice message played back by the device 110 advising of successful atrial fibrillation detection may prompt the patient to further action. For example, the message may inform the patient that atrial fibrillation was detected and advise the patient of the appropriate action to be taken by the patient if cardioversion is desired. That further action may be to reprogram the defibrillator into the patient activated mode by using switch 118 and then to depress switch 120 to transmit another sequence command to cause a patient activated intervention sequence to be initiated. Alternatively, the defibrillator may be originally programmed so that reprogramming would not be necessary, only requiring switch 118 to be depressed again to initiate therapy. With either approach, it is preferred and desirable, although not absolutely necessary, to repeat atrial fibrillation detection before the attempted cardioversion. Of course, at each stage of the redetection and cardioversion process, suitable status messages may be generated for audible speech playback by device 110 to keep the patient informed.

Figure 2:
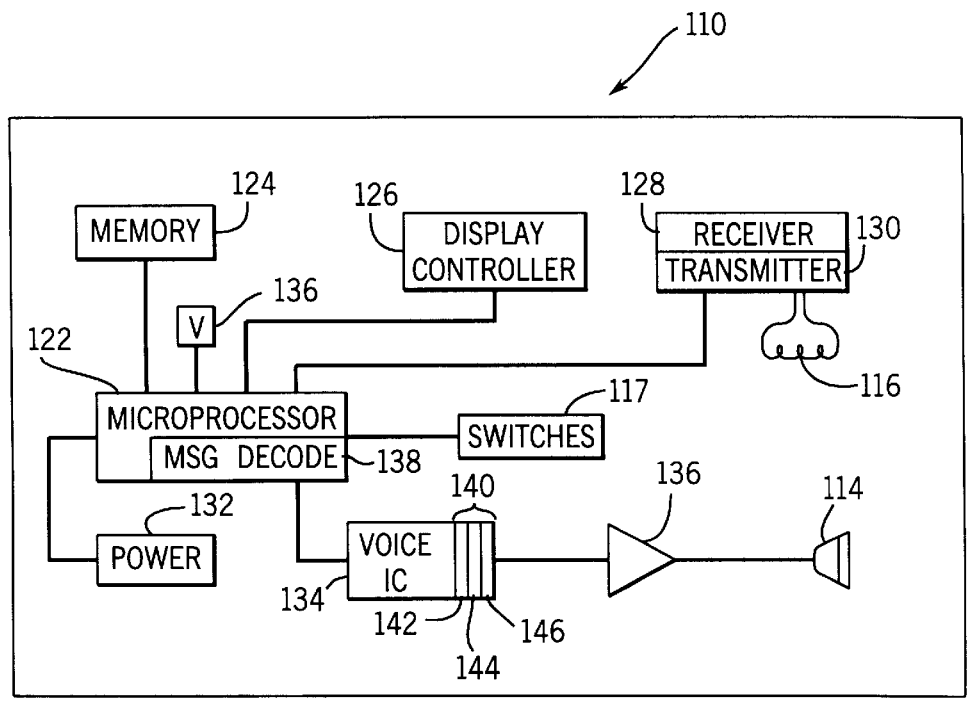
FIG. 2 is a block diagram of a portable communication device which may be used in practicing the present invention.

FIG. 2 is a block diagram of the communication device 110. It includes a microprocessor 122, a first memory 124, a display controller 126, a receiver 128 and transmitter 130, the coil antenna 116, the switches 117, and a battery power source 132. The device 110 further includes a voice integrated circuit 134, an audio amplifier 136, and the speaker 114.

The microprocessor 122 controls the overall functioning of the device 110 by performing operations defined by operating instructions stored in memory 124. The instructions stored in memory 124 preferably include instructions defining a communication protocol compatible with the implantable device 30. The instructions further define a message decoder stage 138 which decodes the acknowledgment and status messages received from the defibrillator 30. The display controller 126 controls the LED 112 and the LCD 114 of the communication device 110 in a manner known in the art. The receiver 128 and transmitter 130 are controlled by the microprocessor 122 for communicating with the receiver/transmitter 102 of the implanted device 30 when required.

Whenever the transmitter 130 sends a command to the implanted device 30, it will expect an acknowledgment from the implanted device that the command was received and is being acted upon. When the acknowledgment is received by receiver 128, the display controller under control of the microprocessor 122 causes the LED 112 to light-up so as to be readily discernible. To further that end, the LED 112 may be caused to blink on and off by the display controller 126. Also a short message may also be displayed on the LCD 113 to further indicate that the command was received and the type of command or mode selection made. All of the foregoing provides positive feedback to the patient when making an external command not previously available in the prior art. This positive feedback includes both an acknowledgment that the command was reached and a description of the task being performed responsive to the command.

The message decoder 138, voice integrated circuit (IC) 134, amplifier 136 and speaker 114 produce the audible voice or speech messages responsive to the acknowledgment messages received from the defibrillator 30. The voice IC 134 may be, for example, the ISD 33240 manufactured by Information Storage Devices. It includes an addressable memory 140 which has a plurality of addressable memory locations. Three such memory locations 142, 144, and 146 are shown for illustrative purposes. Each location is a nonvolatile memory to provide zero-power message storage. Voice signals are stored directly into the memory 140 in their natural form. However, digital integrated circuits may be used as well without departing from the present invention. The amplifier 136, which may be a National Semiconductor LM4860M, amplifies the output of the voice IC 134 to a level suitable to drive speaker 114 at a level to render the voice messages readily audible.

When a message is received by the receiver 128, the decoder 138 decodes the message to determine if a corresponding voice signal message is stored in memory 140. If there is, the decoder 138 addresses the memory to cause the corresponding prestored voice message to be generated and amplified so as to be heard by the patient.

While a particular embodiment of the present invention has been shown and described, modifications may be made. Hence, it is therefore intended in the appended claims to cover all such changes and modifications which fall within the true spirit and scope of the invention.

What is claimed is:

1. An atrial defibrillation system comprising:
   an implantable atrial defibrillator including an atrial fibrillation detector for detecting atrial fibrillation and a cardioverter for cardioverting the atria of a heart, the implantable atrial defibrillator further including a receiver for receiving commands from an external nonimplanted transmitter; and
   a nonimplantable communication device including a transmitter for transmitting a first command to the receiver for activating only the atrial fibrillation detector to cause the atrial fibrillation detector to detect for atrial fibrillation and wherein the cardioverter is not activated in response to the detection of atrial fibrillation unless a further command is transmitted from the nonimplantable communication device to the receiver in the implantable atrial defibrillator.

2. A defibrillation system as defined in claim 1 wherein the implantable atrial defibrillator liner includes a transmitter for transmitting an acknowledgment message upon receiving the first command and wherein the communication device includes a receiver for receiving the acknowledgment message transmitted by the atrial defibrillator transmitter.

3. A defibrillation system as defined in claim 1 wherein the implantable atrial defibrillator includes a transmitter for transmitting a status message indicative of detected atrial fibrillation and wherein the communication device includes a receiver for receiving the status message and means for providing a perceptible indication responsive to receipt of the status message.

4. A defibrillation system as defined in claim 3 wherein the communication device transmitter further includes means for transmitting a further command to the atrial defibrillator receiver and wherein the atrial defibrillator includes means responsive to receipt of the further command to cause the atrial fibrillation detector to redetect for atrial fibrillation and the cardioverter to cardiovert the atria responsive to redetection of atrial fibrillation.

5. An atrial defibrillation system comprising:
   an implantable atrial defibrillator including an atrial fibrillation detector for detecting fibrillation of a patient's atria, an atrial cardioverter for applying cardioverting electrical energy to the patient's atria, a receiver for receiving operation commands transmitted from an external transmitter, and a mode selecting stage for causing the defibrillator to operate in a first mode of operation wherein only the atrial fibrillation detector is activated to detect for atrial fibrillation and wherein the cardioverter is not activated if atrial fibrillation is detected or in a second mode of operation wherein the atrial fibrillation detector is activated to detect for atrial fibrillation and the cardioverter is automatically activated for applying cardioverting electrical energy to the patient's atria if atrial fibrillation is detected; and
   a nonimplantable communication device dimensioned to be hand-held and operable by the patient including a transmitter for selectively transmitting a first operation command to cause the mode selector stage to render the implantable atrial defibrillator in the first mode of operation and a second operation command to cause the mode selector stage to render the implantable atrial defibrillator in the second mode of operation.

6. A defibrillation system as defined in claim 5 wherein the implantable atrial defibrillator further includes a transmitter for transmitting atrial fibrillation detection outcome status messages responsive to the atrial fibrillation detector and wherein the nonimplantable communication device includes a receiver for receiving the outcome status messages and an indicator for providing a perceptible indication of atrial fibrillation detection outcome status.

7. A method of operating an atrial defibrillation system including an implantable atrial defibrillator including an atrial fibrillation detector for detecting atrial fibrillation, a cardioverter for cardioverting the atria of a heart, and a receiver for receiving commands transmitted from an external nonimplanted transmitter in a nonimplantable communication device, comprising the steps of:

transmitting a first command from the nonimplantable communication device to the implantable atrial defibrillator; and activating only the atrial fibrillation detector to detect for atrial fibrillation in response to the first command and not automatically activating the cardioverter if atrial fibrillation is detected.

8. The method of claim 7 comprising the additional steps of:

transmitting a further command from the nonimplantable communication device to the implantable atrial defibrillator; and activating the atrial fibrillation detector to redetect for atrial fibrillation and automatically activating the cardioverter to cardiovert the atria in response to redetection of atrial fibrillation in response to the further command.

9. The method of claim 7 wherein the nonimplantable communication device includes a receiver for receiving status messages transmitted from a transmitter in the implantable atrial defibrillator and comprising the additional steps of transmitting a status message indicative of detected atrial fibrillation from the implantable atrial defibrillator to the nonimplantable communication device and providing a perceptible indication in response to receipt of the status message by the nonimplantable communication device.

* * * * *